United States Patent [19]

Cymbaluk

[11] Patent Number: 4,748,290
[45] Date of Patent: May 31, 1988

[54] HYDROGENATION CATALYSTS AND PROCESS

[75] Inventor: Ted H. Cymbaluk, Bartlesville, Okla.

[73] Assignee: Phillips Petroleum Company, Bartlesville, Okla.

[21] Appl. No.: 104,612

[22] Filed: Oct. 5, 1987

Related U.S. Application Data

[62] Division of Ser. No. 826,455, Feb. 5, 1986, which is a division of Ser. No. 682,466, Dec. 17, 1984, Pat. No. 4,659,687.

[51] Int. Cl.$^4$ ................................................ C07C 5/05
[52] U.S. Cl. .................................................... 585/271
[58] Field of Search ........................................ 585/271

[56] References Cited

U.S. PATENT DOCUMENTS

| | | | |
|---|---|---|---|
| 3,322,686 | 5/1967 | Brown et al. | 502/111 |
| 4,226,809 | 10/1980 | Shioyama | 502/113 |
| 4,327,235 | 4/1982 | Nakao et al. | 585/270 |

*Primary Examiner*—Curtis R. Davis
*Attorney, Agent, or Firm*—Phillips E. J.

[57] ABSTRACT

Novel alumina-supported nickel boride catalysts prepared by the borohydride promoted reduction of nickel arsenate are described. Method of catalyst preparation and process for hydrogenation of acetylenic and diolefinic compounds employing the invention catalysts are also described.

8 Claims, No Drawings

HYDROGENATION CATALYSTS AND PROCESS

This application is a division of Ser. No. 826,455, filed 2/5/86, now allowed, which is a division of Ser. No. 682,466, filed 12/17/84, now U.S. Pat. No. 4,659,687.

BACKGROUND OF THE INVENTION

This invention relates to catalysts. In another aspect the invention relates to hydrogenation catalysts. In yet another aspect the invention relates to method for catalyst preparation. In a further aspect, the invention relates to hydrogenation processes.

For a hydrogenation process to be useful on a large scale, catalysts must be available which are readily and inexpensively prepared, give selective reaction, and have high reactivity over an extended period of time. Prior art hydrogenation catalysts employed for the hydrogenation of acetylenic compounds and diolefinic compounds have a variety of drawbacks which prevent their use on a large scale. Thus, for example, catalysts employing platinum or palladium are very expensive; the preparation of catalysts such as Raney nickel is a relatively tedious process. In addition, some hydrogenation catalysts display low reactivity with functionally-substituted compounds. Where prior art hydrogenation catalysts display high reactivity, a frequent problem is poor selectivity to the desired hydrogenated product, due, for example, to double-bond isomerization of the initially formed olefinic product, further reduction of the initially formed olefinic product, and/or undesired side reactions between the hydrogenation catalyst and any functional groups which may be present on the reactant compound (or product olefinic and/or aliphatic compounds).

OBJECTS OF THE INVENTION

An object of the invention is an active, selective catalyst for the hydrogenation of acetylenic compounds and diolefinic compounds.

Another object of the invention is a process to selectively hydrogenate the carbon-carbon triple bond of acetylenic compounds to give cis-olefinic compounds.

Yet another object of the invention is a process to selectively hydrogenate diolefinic compounds to give monoolefinic compounds.

These and other objects of the invention will become apparent from the disclosure and claims herein provided.

STATEMENT OF THE INVENTION

I have discovered that alumina supported nickel boride catalysts prepared by reaction of nickel arsenate compounds with borohydride reducing agents gives highly selective hydrogenation catalysts. The catalysts of my invention are capable of selectively reducing carbon-carbon triple bonds to cis-double bonds as well as reducing diolefins selectively to monoolefins.

DETAILED DESCRIPTION OF THE INVENTION

In accordance with the present invention, a method is provided comprising contacting an alumina-supported nickel arsenate with at least one borohydride compound. The novel alumina supported nickel boride catalyst which results in a selective catalyst for the hydrogenation of acetylenes and diolefins to give olefins.

In accordance with another embodiment of the present invention, an acetylenic compound and hydrogen are contacted in the presence of novel alumina supported nickel boride catalyst prepared as hereinbefore described under conditions suitable to give cis-olefinic product.

In accordance with yet another embodiment of the invention, a diolefin and hydrogen are contacted in the presence of novel alumina supported nickel boride catalyst prepared as hereinbefore described under conditions suitable to give monoolefinic product.

Catalyst

The alumina supports employed to prepare the catalysts of the invention usually contain a major proportion of alumina. Preferred alumina supports contain a substantial proportion of alumina, e.g., at least about 80 percent by weight of alumina, preferably at least about 90 percent by weight alumina. Most preferably, support employed will contain at least about 95 percent by weight of alumina, although still larger proportions of alumina can be used.

The catalyst employed in the practice of the present invention can be prepared by a variety of methods. For example, support can be contacted first by at least one nickel compound convertible to the arsenate, then by at least one reactive arsenic compound to form a supported nickel arsenate, and finally by at least one borohydride compound to convert the arsenate to the boride. Alternatively, at least one nickel compound convertible to the arsenate and at least one reactive arsenic compound can be contacted to produce nickel arsenate, which is then brought into contact with support to produce a supported nickel arsenate, which is finally contacted with at least one borohydride compound to convert the arsenate to the boride. As another alternative, the nickel arsenate can be contacted with at least one borohydride compound prior to contact with the support.

The preferred sequence of contacting is for support to be contacted with at least one nickel compound convertible to the arsenate in a minimum volume of solvent, followed by contact with at least one reactive arsenic compound. In this manner, the nickel arsenate precipitated is well distributed throughout the pores of the support. Finally, the supported nickel arsenate is contacted with at least one borohydride compound to convert the arsenate to the boride.

The conditions under which catalyst components are contacted are not critical. Satisfactory results are obtained by contacting the components at room temperature. Since contact with oxygen is detrimental to the catalyst, it is desirable to prepare and store the catalysts described herein under an inert gas atmosphere, preferably under a hydrogen atmosphere for extended catalyst lifetimes. After the catalyst components have been thoroughly blended, solvent can be removed by reduced pressure distillation to provide a concentrated catalyst slurry or paste for subsequent use.

Suitable solvents for use in the preparation of the catalysts of the invention are solvents which have an appreciable capacity for dissolution of nickel compounds, arsenic compounds and borohydride compounds, as well as the ability to wet the surface of the alumina supports employed in the practice of the invention. Solvents which satisfy the above criteria include, but are not limited to, water, alcohols, ethers (including cyclic ethers) and the like.

Alcohols which are useful have the general formula

R'—OH wherein R' is $C_1$ through $C_{10}$ alkyl, cycloalkyl, aryl, aralkyl or alkaryl. Exemplary alcohols include methanol, ethanol, butanol and the like.

Ethers which are useful have the general formulae

R'—O—R' or $(CR_2)_zO$ wherein each R' is independently defined as above, each R is independently H, $C_1$ through $C_{20}$ alkyl, cycloalkyl, aryl, aralkyl and alkaryl, and z=3 through 11. Preferably, ethers employed in the practice of the invention have about 4 up to about 12 carbon atoms. Exemplary ethers include diethyl ether, diphenyl ether, tetrahydrofuran (THF) and the like.

The volume of solvent employed for catalyst preparation is not critical. However, it must be recognized that extremely large volumes of solvent are undesirable because of the energy required for subsequent solvent removal. In addition, extremely small volumes of solvent are undesirable because insufficient solid/liquid contact may result.

Suitable nickel compounds convertible to the arsenate which are useful in the preparation of catalysts of the invention are compounds which are at least sparingly soluble in the solvents indicated above. Exemplary nickel compounds include, but are not limited to, nickel acetate, nickel fluoride, nickel chloride, nickel bromide, nickel iodide, nickel nitrate, nickel sulfate, nickel acetylacetonate and the like, and mixtures of any two or more thereof.

Suitable reactive arsenic compounds for use in the preparation of catalysts of the invention are compounds which are at least sparingly soluble in the solvents indicated above. Exemplary arsenic compounds include, but are not limited to, arsenic tribromide, arsenic trichloride, arsenic pentafluoride, arsenic trifluoride, arsenic diodide, arsenic triiodide, arsenic pentoxide, arsenic trioxide, arsenic oxychloride, arsenic monophosphide and the like and mixtures of any two or more thereof. Arsenic pentoxide is presently preferred because of its ready availability and proven good performance.

Suitable borohydride compounds for use in the preparation of catalysts of the invention are compounds which are at least sparingly soluble in the solvents indicated above. Exemplary compounds conform to the formula:

$M(BH_4)_n$ where M is a monovalent or divalent cation selected from the group consisting of quaternary ammonium cations ($NR_4'$-, wherein each R' is independently $C_1$ through $C_{10}$ alkyl, cycloalkyl, aryl, aralkyl and alkaryl), alkaline earth metals and alkali metals. Where M is a monovalent cation, n=1. Where M is a divalent cation, n=2. Examples of useful borohydride compounds are lithium borohydride, sodium borohydride, potassium borohydride, magnesium borohydride, calcium borohydride and tetraethyl ammonium borohydride. Presently preferred is sodium borohydride.

Solutions of at least one nickel compound convertible to the arsenate, at least one reactive arsenic compound and at least one borohydride compound are conveniently contacted with alumina support at about room temperature, although contacting may take place at temperatures from about 0° C. up to about 100° C. Any of the numerous techniques known to those skilled in the art for contacting solids and liquids may suitably be employed. The molar ratio of the catalyst components employed can vary over a wide range, with molar ratios of arsenic compound to nickel compound ranging from about 0.1:1 to about 5:1 and borohydride compound to nickel compound ranging from about 1:1 to about 12:1 most commonly being employed.

The proportion of nickel metal combined with the alumina support can vary appreciably, but generally the support will contain at least about 0.1% by weight of the nickel metal, based on the total weight of alumina support plus nickel compound. Generally the support will contain an upper limit of about 40% by weight of the nickel metal, based on the total weight of support plus nickel compound and calculated as nickel metal. Amounts of about 0.2 to about 20% by weight of the nickel metal, calculated as nickel metal and based on the total weight of support plus nickel compound are preferred, with amounts of about 1 to about 10% by weight of the nickel metal, calculated as nickel metal and based on the total weight of support plus nickel compound are especially preferred because excellent catalyst reactivities and product selectivities are obtained.

Substrate

Substrates useful in the practice of the present invention are acetylenic compounds and diolefinic compounds. Broadly, any compound with acetylenic or diolefinic unsaturation is contemplated to be within the scope of the invention. Generally, an acetylenic compound employed in the practice of the invention will have at least 4 carbon atoms up to about 40 carbon atoms or more. Diolefinic compounds employed in the practice of the invention will generally have at least 5 carbon atoms up to about 40 carbon atoms or more.

In addition to acetylenic and diolefinic hydrocarbons, the catalysts of the invention also find use in the hydrogenation of halide-substituted acetylenic compounds. Preferred halides are chloride, bromide and iodide, with the bromide being most preferred.

Preferred acetylenic compounds for use in the hydrogenation process of the present invention are defined by the formula:

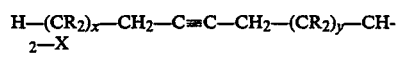

$H—(CR_2)_x—CH_2—C≡C—CH_2—(CR_2)_y—CH_2—X$ wherein x is 0 through 20, inclusive, y is 1 through 20, inclusive, each R is independently H, $C_1$ through $C_{20}$ alkyl, cycloalkyl, aryl and alkaryl, and X is a halogen. These are preferred compounds because the resulting cis-olefinic products are useful intermediates for the preparation of pheromones.

Diolefinic compounds most useful in the practice of the present invention are those diolefins wherein the first double bond of the diolefin is more highly substituted than the second double bond of the diolefin. In accordance with the invention, the second double bond, i.e., less highly substituted double bond, is selectively hydrogenated compared to the first double bond. Thus, for example, 4-vinyl-cyclohexene is converted selectively into 4-ethyl-cyclohexene; isoprene can be converted selectively into 2-methyl-1-butene; piperylene can be converted selectively into 2-pentene; and so on.

Hydrogenation

Hydrogenation in accordance with the present invention can be carried out on any of the acetylenic compounds or diolefinic compounds previously described. It should of course also be recognized that hydrogenation of, for example, an acetylenic halide to give an olefinic halide can be followed by a one-step oxidation as described above to give an olefinic aldehyde. Thus, a wide variety of olefinic products can be prepared according to the invention by converting one functional group to another either before or after the inventive hydrogenation step is carried out.

In accordance with the present invention, acetylenic compounds or diolefinic compounds are selectively hydrogenated to give cis-olefinic products or monoolefinic products, respectively. Selective hydrogenation refers to the amount of hydrogen consumed in the hydrogenation reaction, i.e., one mole of hydrogen per mole of acetylenic compound or diolefin compound to give an olefin (to the substantial exclusion of the consumption of two moles of hydrogen per mole of acetylene or diolefin to give an aliphatic compound); to the orientation of hydrogen addition across the acetylenic triple bond where an olefinic product is obtained; and to the presence or absence of double-bond isomerization in the olefinic product obtained upon addition of one mole of hydrogen to an acetylenic or olefinic compound. Selectivities of at least 90% by weight to cis-olefinic or monoolefinic products are desirable, with less than about 5% by weight of trans-olefinic product (or isomerized monoolefinic product) and less than about 5% by weight of saturated (i.e., aliphatic) product. Preferably, selectivities of at least about 95% by weight of cis-olefinic or monoolefinic products will be obtained, with less than about 3% by weight each of trans-olefinic product (or isomerized monoolefinic product) or saturated product.

Reaction parameters include a preferred reaction pressure of atmospheric to about 500 psig, although most any pressure can be employed. Suitable reaction temperatures include about 0° C. to about 150° C. with temperature preferably maintained between about 20° and about 100° C. Most preferably, a reaction temperature of 30° to about 50° C. will be employed. Reaction time can broadly be 30 minutes to about 8 hours, with 60 minutes to about 120 minutes preferred.

Solvent and substrate can be employed in any suitable ratio as readily determined by one skilled in the art. Suitable ratios are about 10:1 to about 1:10 parts by volume of solvent to substrate. Preferably, for ease of handling and product recovery, solvent and substrate are charged to the reactor in roughly equal volumes.

The total amount of catalyst to be used can be readily determined by one skilled in the art. Preferably, the amount of catalyst employed, expressed as the molar ratio of unsaturated compound charged to the nickel metal in the supported catalyst, ranges from about 1:1 to about 300:1. Most preferably a molar ratio ranging from about 5:1 to about 100:1 is used, for most efficient use of catalyst and high product selectivities.

Hydrogen is generally fed on demand, i.e., as it is taken up by the reaction mixture. Thus, for example, where reaction is carried out at 120 psig, reactor pressure may be allowed to drop to about 60 psig, then the pressure will be returned to about 120 psig by introducing more hydrogen. Alternatively, reaction may be run at atmospheric pressure with continuous hydrogen uptake from a manometer assembly as hydrogen is consumed by reaction.

In accordance with a specific embodiment of the invention, it has been discovered that the addition of small amounts of acetone to the hydrogenation reaction mixture leads to improved product selectivities. Small amounts of acetone are about 1 mole of acetone per 50 to about 200 moles of unsaturated substrate. Preferably, when employed, about 1 mole of acetone per about 50-100 moles of unsaturated substrate will be charged to the hydrogenation reaction mixture.

Reaction workup consists of catalyst removal, for example, by filtration, to give a filtrate, and solvent removal from the filtrate by such techniques as flash distillation, distillation under reduced pressure, and the like.

EXAMPLE I

Catalyst Preparation

Catalyst A

This example illustrates the preparation of an alumina-supported nickel arsenate-boride catalyst in accordance with this invention. 13.2 grams ($4.54 \times 10^{-2}$ moles) of $Ni(NO_3)_2.6H_2O$ were dissolved in 20 mL of $H_2O$. A separate solution was prepared by dissolving 3.6 grams of $As_2O_5$ ($6.2 \times 10^{-2}$ moles) in water so as to provide 75 mL of an aqueous solution. The two solutions were combined and mixed well with 15 grams flame-hydrolyzed alumina (surface area: 120m$^2$/g, marketed by Degussa Corporation, Teterboro, N.J. The pH of the mixture was raised from an initial value of about 2 to about 7-8 by addition of about 30 mL 50% aqueous $NH_3$. After standing overnight, the mixture was diluted with water and filtered. The collected precipitate of nickel arsenate was washed several times with water and then dried at about 200° F. for about 3 hours. To the dried precipitate were added first about 40 mL of degassed methanol and then, pelletwise, 1.82 grams of $NaBH_4$ (marketed by Alpha Corporation, Collierville, Tenn.). The slurry turned black with evolution of heat and gases. The slurry was stirred for about 30 minutes and stored under hydrogen.

Catalyst B

Another method of preparing the alumina-supported nickel arsenate-boride catalyst of this invention comprises the steps of impregnating alumina with an aqueous solution of $(Ni(NO_3)_2$, and then allowing an aqueous solution of $As_2O_5(H_3AsO_4)$ to slowly flow through the Ni-impregnated alumina. The thus treated material was rinsed with water and dried at about 60° C. in vacuum for about 5 hours. Then 40 mL of methanol and, pelletwise, 1.0 g. of $NaBH_4$ were added to the dried nickel arsenate impregnated alumina (weight: 14.6 grams). After stirring for 20 minutes, during which heat and gas evolution occurred, an additional amount of 1.0 gram $NaBH_4$ was added to the system. This catalyst material was stored under $H_2$.

Catalyst C

A silica-supported nickel arsenate-boride control catalyst was prepared as follows. 13.2 grams of $Ni(NO_3)_2.6H_2O$ were dissolved in 10 mL of $H_2O$. A second solution was prepared by dissolving 3.6 g $As_2O_5$ in 20 mL of $H_2O$ with stirring and heating. The two solutions were combined and mixed with 15 g Hi-Sil silica (surface area: about 60 m$^2$/g; marketed by PPG Industries, Pittsburgh, Pa.). The impregnated silica was dried at 260° F. for 2 hours. To the ground, dried material were added 80 mL of methanol and, 1.7 grams of NaBH$_4$ pellets with stirring. The mixture was allowed to stand overnight.

Catalyst D

A control catalyst was prepared essentially in accordance with the procedure for Catalyst A, except that the initial nickel nitrate solution contained 13.2 grams of Ni(NO$_3$)$_2$.6H$_2$O plus 3.0 grams of Fe(NO$_3$)$_3$.9H$_2$O.

EXAMPLE II

This example illustrates the selective hydrogenation of 2-hexyne to 2-hexene in the presence of supported nickel arsenate-boride catalyst compositions A, B, C and D. Mixtures of 2–3 mL of 2-hexyne, 100 mL of n-pentane and several grams of the catalyst materials prepared as described in Example I were pressured with hydrogen gas to about 300 psig and then heated. Product samples were withdrawn after various time intervals and analyzed by gas chromatography. Pertinent process conditions and results are summarized in Table I.

TABLE I

| Run | Catalyst | Temp. (°F.) | Run Time (hr.) | % Conv. of 2-hexyne | %-Selectivity[1] to 2-Hexene |
|---|---|---|---|---|---|
| 1 (Invention) | A | 149 | 1 | 13 | 100 |
| | A | 149 | 2 | 26 | 100 |
| | A | 149 | 3 | 35 | 100 |
| | A | 149 | 4.5 | 51 | 100 |
| 2 (Invention) | A | 141–160 | 1 | 67 | — |
| | A | 130 | 1.5 | 91 | — |
| | A | 140 | 2 | 100 | 95[2] |
| 3 (Invention) | A | 117 | 7 | 100 | 93 |
| 4 (Invention) | B | 127–151 | 2 | 100 | 95 |
| 5 (Control) | C | 121–149 | 2 | 0 | — |
| 6 (Control) | C | 125–148 | 1 | 0 | — |
| 7 (Control) | C | 213–236 | 2 | 40 | 85 |
| 8 (Control) | D | 112 | 0.5 | 0 | — |

[1] $\frac{\% \text{ 2-hexene yield}}{\% \text{ 2-hexyne conversion}} \times 100$
[2] yield of cis-2-hexene: 93%; yield of trans-2-hexene: 2%;
[3] small amount of acetone present; yield of cis-2-hexene: 83%; yield of trans-2-hexene: 10%

Data in Table I clearly show that unexpectedly only the alumina-supported nickel arsenate-boride catalyst was an active alkyne hydrogenation catalyst at about 150° F. The silica-supported nickel arsenate-boride catalyst C was not active at 150° F. At 210°–240° F., it became somewhat active, however, with a markedly lower 2-hexene selectivity. Surprisingly, an alumina-supported nickel arsenate-boride catalyst containing minor amounts of Fe (Catalyst D) was not an active alkyne hydrogenation catalyst.

EXAMPLE III

In this example the hydrogenation of 4-vinylcyclohexene (VCH; 2 mL 4-VCH in 100 mL n-pentane) in the presence of several grams of Invention Catalyst A is described. Conversion of 4-VCH was 77% as 137° F./330 psig after about 7 hours. In another test carried out at about 260° F., conversion of 4-VCH after 3 hours was 100%, with the following product selectivities: 50% to 4-ethylcyclohexene, 21% to 2-ethylcyclohexene and 29% to ethylcyclohexane. These tests show that the alumina-supported nickel arsenate-boride catalyzes the hydrogenation of 4-vinylcyclohexene to primarily 4-ethylvinylcyclohexene.

A third 4-VCH hydrogenation test employing Invention Catalyst A was carried out with a small amount of acetone present. 4-VCH conversion after about 20 hours at 186° F. was 100%, with the following product selectivities: 72% to 4-ethylcyclohexene, 12% to 2-ethylcyclohexene and 5% to ethylcyclohexane. Another 4-VCH hydrogenation test at 190° F. with small amounts of acetone present resulted in 96% 4-VCH conversion, 86% selectivity to 4-ethylcyclohexene, 0% selectivity to 2-ethylcyclohexene and 4% selectivity to ethylcyclohexane after about 4–5 hours. These tests demonstrate the beneficial effect of small amounts of acetone on the selectivity to 4-ethylcyclohexene in the hydrogenation of 4-vinylcyclohexene on an Al$_2$O$_3$-supported nickel arsenate-boride catalyst.

EXAMPLE IV

This example illustrates the hydrogenation of an alkynyl bromide C$_4$H$_9$—C≡C—C$_{10}$H$_{20}$Br (1-bromo-hexadecyne; prepared at Phillips Petroleum Company, Research Center, Bartlesville, Okla.) in the presence of alumina-supported nickel arsenate-boride catalyst.

In one run, 20 grams of C$_4$H$_9$—C≡C—C$_{10}$H$_{20}$Br, 5 g of alumina-supported nickel arsenate/boride catalyst A (stored under H$_2$), 100 mL of n-hexane and 0.05 g acetone were charged to a stirred 1-liter autoclave, which was flushed with N$_2$ and subsequently with H$_2$. Hydrogen gas was added to give a total pressure of 200 psig. The reactor contents were stirred and heated to about 64°–85° C. during a period of about 30 minutes. More H$_2$ was added so as to provide a pressure of about 150–185 psig and the temperatures was allowed to rise to about 100° C. After about 80 minutes at 100° C., the reactor was cooled, and the reaction product was analyzed by gas chromatography. Conversion of the alkynyl bromide was 100%. Selectivity to cis-C$_4$H$_9$—CH═CH—C$_{10}$H$_{20}$Br was 92% and to trans-C$_4$H$_9$—CH═CH—C$_{10}$H$_{20}$Br was 5%.

In a second run, 5 grams of Invention Catalyst A, 100 grams of C$_4$H$_9$—C≡C—C$_{10}$h$_{20}$Br, 100 mL of hexane and 5 mL of t-butanol were placed in the stirred autoclave, which was flushed with N$_2$ and then h$_2$. H$_2$ was added so as to pressurize the autoclave to 100 psig. The reaction mixture was kept at about 65°–90° F. for about 30 minutes and then at about 90°–105° F. for about 2 hours. Hydrogen was periodically added so as to provide a pressure of about 60–100 psig. Conversion was 100%; selectivities were about 93–95% to cis-C$_4$H$_9$—CH═CH—C$_{10}$H$_{20}$Br, 2–4% to trans C$_4$H$_9$—CH═CH—C$_{10}$H$_{20}$Br and about 3% to saturated C$_{16}$H$_{33}$Br.

The examples have been provided merely to illustrate the practice of my invention and should not be read so as to limit the scope of my invention or the appended claims in any way. Reasonable variations and modifications, not departing from the essence and spirit of my invention, are contemplated to be within the scope of patent protection desired and sought.

I claim:

1. A process for preparing a monoolefinic compound from a diolefinic compound comprising contacting a diolefinic compound with hydrogen under hydrogenation conditions in the presence of a catalyst prepared by contacting an alumina supported nickel arsenate with at least one borohydride compound; wherein said at least one borohydride compound conforms to the following formula:

$$M(BH_4)_n$$

wherein M is a monovalent or divalent cation selected from the group consisting of:
- NR′$_4$; wherein each R′ is independently C$_1$ through C$_{10}$ alkyl, cycloalkyl, aryl, aralkyl and alkaryl,
- alkali metals, and
- alkaline earth metals;

wherein n=1 if M is a monovalent cation and n=2 if M is a divalent cation.

2. A process in accordance with claim 1 wherein said alumina-supported nickel arsenate is prepared by contacting a predominantly alumina support with:
(1) at least one nickel compound convertible to the arsenate, and
(2) at least one reactive arsenic compound, to produce an alumina supported nickel arsenate.

3. A process in accordance with claim 1 wherein said diolefinic compound has at least 5 up to about 40 carbon atoms.

4. A process in accordance with claim 3 wherein the first double bond of said diolefinic compound is more highly substituted than the second double bond of said diolefinic compound.

5. A process in accordance with claim 4 wherein said diolefinic compound is 4-vinylcyclohexene.

6. A process in accordance with claim 1 wherein the nickel metal content of said alumina supported nickel arsenate ranges from about 0.1 to about 40 wt. % based on the total weight of alumina support plus nickel compound.

7. A process in accordance with claim 1 wherein the molar ratio of said diolefinic compound to nickel metal in said catalyst is about 1:1 to about 300:1.

8. A process in accordance with claim 1 wherein the contacting of said diolefinic compound is carried out in the further presence of small amounts of acetone.

* * * * *